United States Patent [19]
Slininger et al.

[11] Patent Number: 6,107,247
[45] Date of Patent: Aug. 22, 2000

[54] BIOLOGICAL CONTROL OF SPROUTING IN POTATOES

[75] Inventors: Patricia J. Slininger, Metamora; Karen D. Burkhead, East Peoria; David A. Schisler, Morton; Rodney J. Bothast, East Peoria, all of Ill.

[73] Assignee: The United States of America as represented by the Secretary of Agriculture, Washington, D.C.

[21] Appl. No.: 09/257,730

[22] Filed: Feb. 25, 1999

[51] Int. Cl.$^7$ .............. A01N 63/00; C12N 1/00; C12N 1/20
[52] U.S. Cl. ............ 504/117; 424/93.4; 424/93.47; 435/822; 435/874; 435/876
[58] Field of Search ............... 424/93.4, 93.47; 435/822, 874, 876; 504/117

[56] References Cited

U.S. PATENT DOCUMENTS

| | | | |
|---|---|---|---|
| 4,242,120 | 12/1980 | Manankov M.K. | 71/89 |
| 4,849,008 | 7/1989 | Schroth et al. | 435/876 |
| 5,129,951 | 7/1992 | Vaughn et al. | 71/122 |
| 5,139,562 | 8/1992 | Vaughn et al. | 71/88 |
| 5,436,226 | 7/1995 | Lulai et al. | 504/291 |
| 5,510,253 | 4/1996 | Mitsky et al. | 435/172.3 |
| 5,552,315 | 9/1996 | Slininger et al. | 435/253.3 |
| 5,635,452 | 6/1997 | Lulai et al. | 504/324 |
| 5,783,411 | 8/1998 | Schisler et al. | 435/34 |

OTHER PUBLICATIONS

Farag et al. Acta Phytopatol Entolmol Hung. 1986, 21 (1–2), 115–122.
ATCC Catalogue. Bacteria and Bacteriophages. 19th edition. 1996. pp. 133 and 260.
Colyer et al. Plant Disease, Aug. 1984, vol. 68, pp. 703–706.
Elson et al. Plant Disease, Jun. 1997, vol. 81, pp. 647–652.
Munzer M. DLZ., May 1980, vol. 31, No. 5, p. 689.
Luther et al. Radiat. Phys. Chem. I990, vol. 36, No. 5, pp. 657–660.

*Primary Examiner*—Irene Marx
*Assistant Examiner*—Vera Afremova
*Attorney, Agent, or Firm*—M. Howard Silverstein; Curtis P. Ribando; John D. Fado

[57] ABSTRACT

Sprouting in stored potatoes is suppressed with sprout control agents of bacterial origin. These agents are typically applied to the potato surfaces as whole culture broths and they prevent softening and necrosis of the tuber. In a preferred embodiment of the invention, selected isolates also have the secondary effect of Fusarium dry rot control.

10 Claims, No Drawings

BIOLOGICAL CONTROL OF SPROUTING IN POTATOES

BACKGROUND OF THE INVENTION

1. Field of the Invention

This invention relates to the use of microorganisms or elaboration products thereof for the suppression of sprouting in stored potatoes.

2. Description of the Prior Art

In the North America alone, the total annual potato production is 393 million cwt. In excess of 70% of that crop is stored, representing a $1.4 billion investment. Typically, tubers are harvested, allowed to suberize (i.e. allow the "skin" or periderm layer to toughen) at warm temperature ~15° C. for about 10 days, then gradually cooled down to the storage temperature of about 7–13° C. For the first 1–2 months after harvest, the tubers remain dormant and exhibit little inclination to sprout. However, after this period, the tendency for the tubers to sprout results in numerous deleterious effects. These include a loss of fresh weight, the conversion of starch to sugars, and a decrease in the quality and appearance of tubers sold fresh. Sprouts and the surrounding tissue also contain elevated levels of toxic glycoalkaloids, which are destroyed by cooking. Because of the adverse effects caused by sprouting, sprout control is required for the 54% of potato crop used for process potatoes.

Low storage temperatures around 3° C. are an effective sprout deterrent, but process potato quality is lost at very low temperatures due to the high rate of accumulation of soluble sugars. Thus, because of processing demands, over 54% of the annual potato harvest must be stored at 7° to 13° C., a temperature range above that needed for ideal sprout control ("Design and Managment of Storages for Bulk, Fall-crop Irish Potatoes", *ASAE Standards*, St. Joseph, Mich., 1990). If storage temperatures exceeding 3° C. are required, chemical sprout inhibitors must be applied to control sprouting. Sprout inhibitors can be applied during the growing season, after storage, or as potatoes are moved into storage. Two chemicals are used in the United States. Maleic hydrazide, a systemic compound, must be applied to the plant foliage before harvest and is not amenable to application on stored potatoes (Yada et al., "The Effect of Maleic Hydrazide (Potassium Salt) on Potato Yield, Sugar Content and Chip Color of Kennebec and Norchip Cultivars", *Am. Potato J.*, 68:705–709, 1991). Moreover, the timing of this foliar application is critical to its success. Consequently, CIPC (Chlorpropham; 1-methylethyl-3-chlorophenylcarbamate) is the most widely used sprout inhibitor world-wide. It can be applied as a dust, granule, spray or dip as potatoes enter storage, or most effectively as a fog during storage, but suitable ventilation systems are required (Orr et al., "Design and Performance of a Test Facility for Evaluating Potato Sprout Inhibitors", *Transactions of the ASAE*, 37(6):1899–1905, 1994; Leach, "Quality of Stored Potatoes Improved by Chemical Treatment", *Am. Potato J.*, 55:155–159, 1978; Duncan et al., "Methods for Controlling Sprouting in Potatoes", *Aspects of Applied Biology*, 33:189–196, 1992). CIPC is a mitotic inhibitor known to have an inhibitory effect on wound healing, and for this reason its application is often delayed until after suberization in order to prevent storage rots from gaining access (Duncan et al., "Methods for Controlling Sprouting in Potatoes", *Aspects of Applied Biology*, 33:189–196, 1992). Although irradiation processes inhibit sprouting, they generally have a detrimental effect on the chemical composition of the tuber and lack practicality for application (Leszczynski et al., "Effect of Gamma Irradiation on Potato Quality and Subsequent Production of Chips", *Pol. J. Food Nutr. Sci.*, 1/42 (No.3):61–69, 1992; Hayashi et al., "Identification of Irradiated Potatoes by Electrical Measurements", *J. Food Irradiat.*, Japan, 26:66–72, 1991).

The potato industry has become very dependent on CIPC as the most efficient sprout inhibitor with fewest detrimental side-effects on process potato quality. CIPC is the only synthetic chemical presently registered as a sprout inhibitor for post-harvest application to stored potatoes in the United States. However, CIPC is known to be among the three agrichemicals found in highest concentrations in the diet of the average American (Gartrell et al., "Pesticides Selected Elements, and Other Chemicals in Adult Total Diet Samples, October 1980–March 1982", *J. Assoc. Off. Anal. Chem.*, 69:146–159, 1986), and it comprises over 90% of the total synthetic chemical residues found in U.S. potatoes (Gunderson, J. "FDA Total Diet Study, April 1982–April 1984, Dietary Intakes of Pesticides, Selected Elements, and Other Chemicals", *Assoc. Off. Anal. Chem.*, 71:1200–1209, 1988). Because of its persistence in the environment and potato tissue, concerns about its toxicity have been under review by the Environmental Protection Agency. CIPC is a derivative of ethylurethane, a well-known carcinogen, and it is not known whether CIPC, once ingested, is converted back to this parent compound (Mondy et al., "Effect of Storage Time, Temperature, and Cooking On Isopropyl N-(3-chlorophenol) Carbamate Levels in Potatoes", *J. Agric. Food Chem.*, 40:197–199, 1992). Because of its vulnerable position, the potato industry is in search of alternative agents for sprout control. Natural products less persistent in the environment are among the alternatives being studied in various laboratories (Orr et al., "Design and Performance of a Test Facility for Evaluating Potato Sprout Inhibitors", *Transactions of the ASAE*, 37(6):1899–1905, 1994; Vaughn et al., "Volatile Monoterpenes Inhibit Potato Tuber Sprouting", *Am. Potato J.*, 68:821–831, 1991; Vaughn et al., "Antifungal Activity of Natural Compounds Against Thiabendazole-resistant Fusarium Sambucinum Strains", *J. Agric. Food Chem.*, 42:200–203, 1994).

Vaughn et al., U.S. Pat. No. 5,139,562, and Vaughn et al., U.S. Pat. No. 5,129,951, disclosed that the oxygenated monoterpenes cineole, fenchone and menthol, as well as several aromatic aldehydes and alcohols, including thymol, hydrocinnamaldehyde, cuminaldehyde, salicylaldehyde, cinnamaldehyde, and benzaldehyde, may be advantageously used to inhibit potato tuber sprouting, fresh weight loss, rotting, and fungal growth. Vaughn et al., U.S. Pat. No. 5,129,951, also reported that the aromatic acid, benzoic acid, did not inhibit tuber sprouting.

Lulai et al., U.S. Pat. No. 5,436,226, disclose the use of various jasmonate compounds for controlling sprouting in tubers and for improving their processing qualities.

Lulai et al., U.S. Pat. No. 5,635,452, disclose a method for inhibiting sprouting of potato tubers comprising exposing potato tubers to an aromatic acid, including anisic acid, coumaric acid, gallic acid and mixtures thereof.

In studies of allelopathy, it is well established that microorganisms play an important role in plant growth regulation by producing bioactive products (Putman et al., *The Science of Allelopthy*, John Wiley & Sons, New York, N.Y., 1986; Inderjit et al., "Allelopathy Organisms, Processes, and Applications", *ACS Symposium Series* 58, American Chemical Society, Washington, D.C., 1995). Such products may either stimulate or inhibit plant growth. Natural products derived from microbes have been sought and commercialized as herbicides or plant growth regulators for the protection of agricultural crops. Unlike their synthetic derivatives, such natural products are attractive pest control agents because their persistence in the environment is limited by biological and/or chemical degradation, hence minimizing any risk of ecological disturbance.

SUMMARY OF THE INVENTION

We have now discovered that sprouting in stored potatoes can be suppressed by treating the potatoes with sprout control agents of microbial origin either prior to, or during storage. In the preferred embodiment of the invention, the sprout control agent is a liquid culture of a bacterial agent that can also function to control dry rot disease.

In accordance with this discovery, it is an object of the invention to provide an improved method for suppression of tuber sprouting without necrosis or softening of the tuber.

It is also an object of the invention to provide a safe and environmentally friendly alternative to CIPC as potato sprout inhibitor.

It is a specific object of the invention to control sprouting in stored potatoes by means of naturally-occurring microorganisms.

A more particular object of the invention is to protect potatoes in storage against both dry rot and sprouting damage by treating them once as they enter storage with microorganisms that have been selected for Fusarium dry rot control.

Other objects and advantages of the invention will become readily apparent from the ensuing description.

DEPOSIT OF BIOLOGICAL MATERIAL

Eighteen bacterial isolates were previously obtained by the screening and selection procedures described in Slininger et al., U.S. Pat. No. 5,552,315 and Schisler et al., U.S. Pat. No. 5,783,411, both herein incorporated by reference. These isolates were disclosed in these patents as being useful as antagonists of Fusarium dry rot. Five of the eighteen bacterial antagonists were deposited in the USDA, Agricultural Research Service Patent Culture Collection in Peoria, Ill. under the terms of the Budapest Treaty on Feb. 22, 1993, including *Pantoea agglomerans* NRRL B-21048, *Pseudomonas corrugata* NRRL B-21049, *Enterobacter cloacae* NRRL B-21050, *Pseudomonas corrugata* NRRL B-21051, and *Pseudomonas fluorescens* bv.V NRRL B-21053. Five additional strains were deposited in the Agricultural Research Service Patent Culture Collection under the terms of the Budapest Treaty on May 26, 1993, including Enterobacter sp. NRRL B-21101, *Pseudomonas fluorescens* bv.I NRRL B-21102, Enterobacter sp. NRRL B-21103, Pantoea sp. NRRL B-21104, and Pseudomonas sp. NRRL B-21105. Eight additional strains were deposited in the Agricultural Research Service Culture Collection under the terms of the Budapest Treaty on Aug. 30, 1993, including *Pseudomonas fluorescens* NRRL B-21128, *Pseudomonas corrugata* NRRL B-21129, Enterobacter sp. NRRL B-21132, *Pseudomonas fluorescens* bv.V NRRL B-21133, *Pseudomonas fluorescens* bv.V NRRL B-21134, *Pseudomonas fluorescens* bv.V NRRL B-21135, *Pseudomonas corrugata* NRRL B-21136 and *Pseudomonas fluorescens* bv.V NRRL B-21137.

DETAILED DESCRIPTION OF THE INVENTION

In the preferred embodiment of the invention, the sprout control agents of microbial origin contemplated herein are whole culture broths containing cultivated microbial cells, the metabolized fermentation medium, and any products elaborated by the cells into the fermentation medium. The examples below present experimental evidence that the isolated cells contribute to sprout control, and to a limited extent, so does the cell-free metabolized fermentation medium. However, significantly greater benefit in sprout suppression is achieved by use of the whole culture broth rather than any component individually. The term "sprout control agent" is used herein to refer to a whole culture broth or any component thereof that includes bacterial cells and metabolites that are effective in suppressing potato sprouting during storage. The expression "sprout-suppressing bacterial isolate" refers to any bacterial isolate that can be cultivated to produce a "sprout control agent". Preferred bacterial isolates for use in the invention are the deposit strains listed above.

Maintenance and preparation of the bacterial isolates for application in sprout control involve conventional microbiological techniques. The isolates may be maintained by storing as slant cultures at low temperatures (ca. 5° C.), by storing in aqueous glycerol at −80° C., or by lyophilizing and storing at −10° C.

The isolates would typically be grown in aerobic liquid cultures on media which contain sources of carbon and nitrogen, and inorganic salts assimilable by the microorganism and supportive of efficient cell growth and metabolism. Preferred carbon sources are hexoses such as glucose but other assimilable sources include glycerol, amino acids, xylose, etc. Many inorganic and proteinaceous materials may be used as nitrogen sources in the growth process. Preferred nitrogen sources are amino acids and urea but others include gaseous ammonia, inorganic salts of nitrate and ammonium, vitamins, purines, pyrimidines, yeast extract, beef extract, proteose peptone, soybean meal, hydrolysates of casein, distiller's solubles, and the like. Among the inorganic minerals that can be incorporated into the nutrient medium are the customary salts capable of yielding calcium, zinc, iron, manganese, magnesium, copper, cobalt, potassium, sodium, molybdate, phosphate, sulfate, chloride, borate, and like ions.

For most organisms contemplated to be within the scope of the invention, cell growth can be achieved at temperatures between 1° C. and 40° C., with the preferred temperature being in the range of 15°–35° C. The pH of the nutrient medium can vary between 4 and 9, but the preferred operating range is 6–8. Ordinarily, cultures reach stationary phase and are ready to harvest within 20–96 hours after inoculation, but the exact timing of the harvest will depend on the strain and the nutrient and growth conditions applied. The harvest time can be chosen based on one or more readily measurable culture conditions associated with prior observation of sprout suppressive bioactivity of the product, including for example, cell yields and the depletion of substrates.

Optimal conditions for the cultivation of the isolates will, of course, depend on the particular strain. However, a person of ordinary skill in the art would be able to determine essential nutrients and growth conditions required by a particular strain to achieve optimum expression of sprout suppression functionality. Likewise, it would be within the skill of a person in the art to determine the optimal cultivation conditions if the isolates are also intended to be bifunctional, that is, to both suppress potato sprouting and also inhibit dry rot.

Once harvested, the culture can be applied by any conventional method to the surfaces of potato tuber material, to include without limitation whole potato tubers, potato tuber parts, or seed tubers. For example, the culture is most likely to be applied directly as an aqueous spray or dip, or as a spray or dip reconstituted from a dry form, such as a wettable powder. In yet another embodiment, the dried culture can be applied as a dust. Formulations designed for these modes of application will usually include a suitable liquid or solid carrier together with adjuvants, such as wetting, sticking agents and the like to promote ease of application and maximum expression of sprout biocontrol and optionally, dry rot biocontrol function. Polysaccharides such as starch and cellulose, etc. and derivatives thereof are contemplated for inclusion in these formulations as carriers and sticking agents.

The expressions "an effective amount" and "a suppressive amount" are used herein in reference to that quantity of sprout control agent that is necessary to obtain a reduction in the amount of sprouting (and optionally dry rot proliferation) relative to that occurring in an untreated control under suitable conditions of treatment as described herein. The rate of application of the harvested culture will typically be in the range of 0.05 to 2 ml of harvested culture volume per 8 oz. potato. On a cell concentration basis, the rate of application should be at least about $1\times10^8$ viable cells/ml and preferably at least $1\times10^9$ viable cells/ml. Even better results are obtained at concentrations exceeding $1\times10^{10}$ viable cells/ml. The optimum dosage will depend on a number of factors, such as the size of the potato, the bacterial strain, and the associated cultivation conditions of the bacteria strain. Dry rot control can be achieved at application rates of about $1\times10^3$ to about $1\times10^{10}$ viable cells/ml and preferably from about $1\times10^6$ to about $1\times10^9$ viable cells/ml. The skilled artisan would be able to determine the dosage of a given whole culture broth required for optimum expression of sprout and dry rot biocontrol activities.

If dry rot control is a consideration, then the treatment with the sprout control agent should occur prior to, or during the very early stages of, storage when potato wounds resulting from the harvest and transport process are not yet healed and are susceptible to infection. Under some circumstances dry rot infection may not be a threat. Examples include potatoes that have undergone wound healing, potatoes that have been treated with an effective chemical fungicide, and potato cultivars that are resistant to dry rot infection. If dry rot is not a threat, the treatment may be effectively applied anytime during storage, but before the onset of sprouting. The potatoes can be stored under typical commercial storage house conditions: 4–20° C. (preferably 8–15° C.) and 80–100% relative humidity (preferably 85–95% relative humidity).

The following examples are intended only to further illustrate the invention and are not intended to limit the scope of the invention which is defined by the claims.

EXAMPLE 1

Potato Sprout Bioactivity Exerted by Six Deposit Strains and the Impact of Cultivation Conditions Experiment Design.

Six of the 18 isolates for potato dry rot control were identified as the most commercially promising by the method of Slininger et al. (1994) [Two-dimensional Liquid Culture Focusing: a Method of Selecting Commercially Promising Microbial Isolates with Demonstrated Biological Control Capability. In: M. H. Ryder, P. M. Stephens, and G. D. Bowen (eds.), Improving Plant Productivity with Rhizosphere Bacteria, 3rd International Workshop on Plant Growth-Promoting Rhizobacteria, Adelaide, S. Australia. CSIRO Division of Soils: Glen Osmond. p. 29–32; and U.S. Pat. No. 5,783,411] as follows: NRRL-B-21050 (*Enterobacter cloacae*, S11:T:07), NRRL-B-21102 (*Pseudomonas fluorescens* bv. I, S22:T:04), NRRL-B-21128 (*Pseudomonas fluorescens* bv. I, S09:Y:08), NRRL-B-21132 (Enterobacter sp., S11:P:08), NRRL-B-21133 (*Pseudomonas fluorescens* bv. V, S11:P:12), and NRRL-B-21134 (*Pseudomonas fluorescens* bv. V, S11:P:14). Because of parallel needs for sprout and dry rot disease control in potato storages, the ability of these antagonists, cultivated under a variety of nutritional conditions, to express sprout regulatory bioactivity was investigated.

Culture media.

The six isolates were cultivated on three different liquid media varying widely in nutrient definition and richness: Difco® Sabouraud Maltose broth (SMB), semidefined complete liquid (SDCL), and minimal defined liquid (MDL). The SMB medium was reconstituted as prescribed by Difco®, i.e. 50 g dry SMB per L. The SDCL medium contained 15 g/L glucose, 15 g/L Difco vitamin-free casamino acids, 0.15 g/L tryptophan, and 0.6 g/L cysteine, 0.01 g/L of each purine/pyrimidine (adenine, cytosine, guanine, uracil, thymine), 0.5 mg/L of each of the vitamins (thiamine, riboflavin, calcium pantothenate, niacin, pyridoxamine, and thioctic acid), 0.05 mg/L of each of the additional vitamins (folic acid, biotin, and $B_{12}$), 2 g/L each of $K_2HPO_4$ and $KH_2PO_4$, 0.1 g/L $MgSO_4(7H_2O)$, 10 mg/L NaCl, 10 mg/L $FeSO_4(7H_2O)$, 4.4 mg/L $ZnSO_4(7H_2O)$, 11 mg/L $CaCl_2(2H_2O)$, 10 mg/L $MnCl_2(4H_2O)$, 2 mg/L $(NH_4)_6Mo_7O_{24}(4H_2O)$, 2.4 mg/L $H_3BO_3$, 50 mg/L ethylenediaminetetraacetic acid. The completely defined MDL medium contained 35 g/L glucose, 1.26 g/L urea, 2 g/L each of $K_2HPO_4$ and $KH_2PO_4$, 0.1 g/L $MgSO_4(7H_2O)$, 10 mg/L NaCl, 10 mg/L $FeSO_4(7H_2O)$, 4.4 mg/L $ZnSO_4(7H_2O)$, 11 mg/L $CaCl_2(2H_2O)$, 10 mg/L $MnCl_2(4H_2O)$, 2 mg/L $(NH_4)_6Mo_7O_{24}(4H_2O)$, 2.4 mg/L $H_3BO_3$, 50 mg/L ethylenediaminetetraacetic acid.

Cultivations.

Glycerol stocks of isolates, stored at −80° C. in 10% glycerol were used to inoculate purity streaks which in turn were used to inoculate slants of 1/5 TSA (6 g/L Difco® Tryptic Soy Broth and 15 g/L Difco® Bacto-Agar). Purity streak and slant cultures were incubated at 25° C. for 2–3 days and then refrigerated until use within the week to inoculate precultures. All cultures (25 ml liquid medium in 125-ml flasks) were inoculated (10% v/v from similar 24-h precultures) and incubated for 96 h at 25° C. and 250 rpm (1-inch eccentricity).

Potato treatments.

The Russet Burbank potatoes tubers treated in this experiment had been harvested by Felix Zeloski Farms, Lake Mills, Wis. in October of Trial Season (TS) #1 and stored in Peoria at 8° C. and 85% relative humidity until time of use (ca. 6 weeks), when they were washed with tap water and rinsed with distilled water. Each of the 18 bacterial cultures was sprayed onto eight potatoes at a rate of 0.3 ml per average 57-g tuber (i.e. 0.15 ml per oz. tuber). Half of the spray volume was applied to potatoes, the potatoes were flipped over and the other half of the treatment volume was sprayed. Eight potatoes were similarly sprayed per each control treatment—unfermented SMB, MDL and SDCL and 0.2% (w/v) CIPC. The amount of CIPC applied in this experiment was based on average tuber size and the typical application of 0.01 mg CIPC/g potatoes (i.e. 10 ppm) as recommended for commercial use (Leach, "Quality of Stored Potatoes Improved by Chemical Treatment," *American Potato Journal*, 55:155–159, 1978).

Potato storage and monitoring.

The treatments were sprayed and placed in plastic bags and stored in the dark at 15° C. and 85% relative humidity for a period of four weeks. Sprouting was rated by counting the total number of white sprouts formed on each potato.

Results.

Table I gives the results of the sprout bioassay. Potatoes treated with CIPC had significantly fewer sprouts than those treated with the unfermented media, 6.3 versus 11.5 sprouts per potato, respectively. The sprouting of potatoes did not vary significantly with the three different unfermented media control treatments, indicating that the variation of the media ingredients had no significant impact on sprouting. However, a two-way analysis of variance indicated the following significant sources of variation in the sprouting observed on potatoes treated with the dry rot biocontrol agents: isolate identity ($P<0.0001$), cultivation medium ($P<0.0001$), and the interaction of isolate×cultivation medium ($P<0.03$). In this experiment, potatoes treated with cultures grown on the SDCL medium averaged 6.3 sprouts per potato, which was significantly less than 10.8 or 10.7 sprouts per potato observed for tubers treated with cultures grown on either the MDL or SMB medium, respectively ($P<0.05$ Student-Newman-Kuels (S-N-K) pairwise comparison). Potatoes treated with B-21132 cultures showed significantly less sprouting than those with the unfermented media control and the other five isolates ($P<0.05$ via S-N-K pairwise comparison). The SDCL cultures of strains B-21102 (*Pseudomonas fluorescens* bv.I, S22:T:04), B-21133 (*Pseudomonas fluorescens* bv.V S11:P:12), B-21134 (*Pseudomonas fluorescens* bv.V, S11:P:14) and all three media cultures of strain B-21132 (*Enterobacter cloacae* S11:P:08) significantly reduced sprouting relative to the unfermented media controls and maintained sprouting at a low level, statistically equivalent to that demonstrated by the CIPC treatment. These findings indicate that given appropriate cultivation conditions, at least 4 out of 6 of the commercially promising dry rot biocontrol agents are also capable of significant inhibition of potato sprout growth, a trait adding significantly to their potential market value. It is notable that the SDCL and SMB cultures of B-21050 (S11:T:07) also reduced sprouting by 20–23% compared with the uninoculated media controls in the experiment, even though this reduction was not statistically significant, given the available sample number. The high percentage of sprout suppressive strains among the six isolates tested and the sensitivity of sprout suppressive bioactivity to strain cultivation conditions suggests that it is likely that appropriate modification of growth conditions could render many, or perhaps all 18 of the deposit strains capable of sprout suppression.

EXAMPLE 2

Pilot Demonstration of Potato Sprout Bioactivity by Six Isolates Applied in Fall of Trial Season #2

Experiment design.

Similarly to Example 1, six of the most commercially promising dry rot antagonists were evaluated for sprout regulatory bioactivity as follows: NRRL-B-21050 (*Enterobacter cloacae* S11:T:07), NRRL-B-21053 (*Pseudomonas fluorescens* bv. V P22:Y:05), NRRL-B-21102 (*Pseudomonas fluorescens* bv. I S22:T:04), NRRL-B-21132 (Enterobacter sp. S11:P:08), NRRL-B-21133 (*Pseudomonas fluorescens* bv. V S11:P:12), and NRRL-B-21134 (*Pseudomonas fluorescens* bv. V S11:P:14). This list of strains tested is the same as that of Example 1 except for strain B-21053 (P22:Y:05), which replaced B-21128 (*Pseudomonas fluorescens* bv. I S09:Y:08), the isolate demonstrating the least sprout bioactivity. Each strain was grown 96h in triplicate on two different liquid culture media—MDL (minimal defined liquid) and SDCL (semidefined complete liquid) media as described in Example 1.

Cultivations.

Glycerol stock cultures were maintained and transferred to 1/5 TSA slants as previously described in Example 1, and precultures of each strain were inoculated by sterile loop transfer of cells from slant to 50 ml media in 125 ml flasks closed with silicone sponge plugs. Test cultures (100 ml liquid medium in 500-ml flasks fitted with silicone sponge cap closures) were inoculated to initial optical density (620 nm) of 0.1 absorbance units by transferring an appropriate volume of the corresponding 24-h preculture grown on like medium (SDCL or MDL). All cultures were incubated for 96 h at 25° C. and 250 rpm (1-inch eccentricity).

Potato treatments.

Upon harvest, cultures were transferred to bottles, capped, packed in coolers, and shipped via overnight mail to a test facility in Parma, Id. On the day after arrival, treatments were sprayed onto unwashed Russet Burbank potatoes which had been harvested locally about three weeks prior to use. Each of the 12 cultures was sprayed onto potatoes at a rate of 0.8 ml per each 6–8 oz tuber (i.e. 0.1–0.133 ml per oz). Controls for the experiment included CIPC applied as a thermal fog at 16.6 ppm and no treatment.

Potato storage and assessment.

Three replicates of ~25 potatoes each were stored in mesh bags which were distributed randomly in the bulkhead of a storage bay held at 8° C., 85–95% relative humidity. Sprout length was monitored monthly beginning in February by rating the length of the longest sprout per potato. The definition of the longest sprout length (LSL) rating scale used in Parma was: 0=no peeping or bulging; 1=peeping/bud swelling up to 3 mm; 2=sprouts 4 mm up to 1 cm; 3=sprouts 1 cm up to 3 cm; 4=3 cm up to 5 cm; 5=5 cm or more. Ten tubers were rated from each replicate bag and then destroyed.

Results.

Table II indicates that through four months of storage postharvest (October 30–March 4), all treatments were significantly less sprouted than the untreated control; nine out of twelve biological treatments were significantly less sprouted than the distilled water-treated control; and ten out of twelve biological treatments showed a significant level of sprout control that was statistically equivalent to that of CIPC. Through four months storage, three treatments averaged lower sprout ratings than CIPC: B-21050 (S11:T:07) cultivated in MDL, B-21134 (S11: P:14) cultivated in MDL, B-21133 (S11:P:12) cultivated in SDCL. Relative to the untreated control, sprout reduction by these three cultures ranged 63–77%, compared with 61% by the 16.6 ppm CIPC thermal fog treatment. Ten of 12 biological treatments had 13 to 40% of tubers still not peeping (LSL rating 0) compared with only 6.6% of CIPC-treated tubers not peeping. Nine of 12 biological treatments had high percentages of tubers still suitable for fresh pack (i.e. LSL rating <1), 60–83% compared with 87% and 26.7% for CIPC and untreated controls, respectively. Thus, cultures of all six isolates demonstrated significant sprout control capabilities when grown on at least one of the growth media supplied.

EXAMPLE 3

Pilot Demonstration of Potato Sprout Bioactivity of Six Isolates Applied in Fall of Trial Season #3

Experiment design.

For the trial in the Fall of TS #3, the same treatments were again prepared and evaluated as for the Fall of TS #2, except the culture of B-21132 (S11:P:08) on MDL medium was left out due to limited availability of storage space at the test facility. Isolates were grown on both MDL and SDCL media as described in Examples 1 and 2.

Cultivations.

Bacterial isolates were cultivated as described under Example 2, except that the production culture volume was increased to 600 ml in a 2800-ml Fernbach flask closed with a gauze-covered milk filter.

Potato treatments.

The 11 biocontrol treatments cultivated were harvested and packed in coolers held at 2–6° C. for overnight transport to the test facility in Parma, Id., where they were refrigerated until use. Four days after harvest, the biocontrol agents were applied to unwashed Russet Burbank potatoes which had been harvested locally around two weeks previous to treatment. Each of the 11 cultures was sprayed onto 120 lbs (~234 count) of potatoes at a rate of 0.8 ml per each 8-oz tuber (i.e. 0.1 ml per oz). Controls for the experiment included no treatment, CIPC applied as a thermal fog at 525° F. for 5 minutes to achieve 16.6 ppm weight active ingredient per weight potato, and CIPC (emulsifiable concentrate) applied as a spray at a rate of 10 ppm, typically used to treat "fresh pack" potatoes.

Potato storage and assessment.

Each test and control treatment was stored in a 60-gallon barrel at 8–10° C. and 90–95% relative humidity. Loaded barrels were periodically ventilated: 3 hours fresh air flow at 0.25 scfm followed by 3 hours of no air flow. Sprouts were monitored monthly by removing 60 tubers from each treatment barrel and rating the longest sprout length (LSL) per potato based on the 0–5 rating scale described above. During the final April monitoring, sprout weight percent was assessed for each potato as 100×(total weight of sprouts)/(total sprout+potato weight). LSL ratings are sensitive to differences in treatments having very small sprouts; but as potato sprouting progresses, the sprout weight percent measurement is a more quantitative assessment of the sprouting in potato treatments and is more sensitive to differences in treatments having more developed sprouts. For example, compared to the LSL rating system, the sprout weight percent measurement distinguishes more accurately between potatoes with only one as opposed to numerous long sprouts, or between potatoes with long wispy sprouts versus long bulky sprouts, or between potatoes with 7 cm sprouts versus 5 cm sprouts (both rated as 5 by the LSL scale), and so forth.

Results.

Sprout development was rapid in all of the treatments, and the LSL ratings at each monitoring time in this experiment, far exceeded those taken at corresponding times in the trial of Example 2. As illustration of the difference in sprout potential existing for the two harvest seasons, the mean LSL ratings recorded for 16.6 ppm CIPC/untreated controls on February 4, March 4, and April 7 monitorings of the trial in TS #2 (Example 2) were 0.43/1.3, 1.13/2.87, and 1.33/4.9, respectively, but were 1.37/2.3, 4.15/4.27, and 4.78/4.90, respectively, at similar monitoring times of the trial in TS #3. Because aggressive sprouting was occurring in all treatments monitored especially during March and April, the LSL rating method was not sensitive to differences in the degree of sprouting among treatments, and it was necessary to compare treatments using the more quantitative sprout weight percent measurement. Based on sprout weight percent, Table II indicates that the following seven treatments inhibited sprouting as well as, or better, than the CIPC control and significantly reduced sprouting by 40–63% relative to the untreated control: B-21132 (S11:P:08), B-21102 (S22:T:04), and B-21133 (S11:P:12) strains each grown in MDL medium; B-21050 (S11:T:07) and B-21134 (S11:P:14) each cultivated in either MDL or SDCL medium.

EXAMPLE 4

Relative Sprout Control Performance of Six Isolates As Analyzed Across Two Harvest Years and Two Trial Sites Design of Relative Performance Analysis.

In all, a total of four experiments similar to the two designs noted in Examples 2 and 3, were conducted at Parma and Peoria sites in TS #2 and TS #3. Although the same series of twelve bacterial treatments plus controls were tested, the trials conducted at Peoria and Parma differed from one another in several aspects, including potato source and storage conditions. In order to examine which treatments offered superior sprout suppression overall, regardless of test site differences, relative performance indices (RPI's) were calculated as shown in Table III for each treatment within each site-monitoring The following seven site-monitorings, which yielded significant variation among treatments, were included: Parma Feb., TS #2, Parma Mar. TS #2, Peoria Jan., TS #2, Peoria Feb., TS #2, Parma Mar., TS #3, Parma Apr. TS #3, and Peoria Mar., TS #3. Within a given site-monitoring, treatments having highest RPI values would indicate treatments showing best performance with respect to sprout suppression. For each treatment, seven different RPI's were calculated corresponding to the seven site-monitorings; and an overall RPI was calculated for each treatment as the average of the seven site-monitoring RPI values. Statistical pairwise comparison methods were applied to test for significant differences between overall RPI means.

Fall Trial Season #2 Peoria trial.

In this study, identical treatments were applied to the same harvest of Idaho Russet Burbank potatoes as used for the previously described Parma trial that season. The potatoes, including CIPC-fogged controls, were shipped from Parma to Peoria via ground transportation. For all biological and control treatments, three replicates consisting of twenty-five 6–8 oz-potatoes per replicate were prepared. The Peoria storage conditions were different from the Parma conditions previously described. In Peoria, each replicate was contained in a 16"(L)×12"(W)×4.5"(H) high density polyethylene box with solid bottom and mesh sides (Consolidated Plastics, Inc). The experiment required distributing boxes randomly among six equal stacks of boxes, with 2–4 inches between stacks. The stacks were placed in a 2×3 array on a ventilated pallet and thereby supported ~6" above the floor and drain of the Percival® incubator. The potatoes were stored at 10–11.5° C. (compared to 8° C. in Parma) and 90–95% relative humidity from November 25 through March. Potatoes were monitored nondestructively on a monthly basis, beginning in January, using the LSL (0–5) rating method previously described (Example 2).

Fall Trial Season #3 Peoria Trial.

Biological and control treatments were prepared and applied similarly to those tested at Parma, as described in Example 3. However, TS #3 Parma and Peoria trials differed by potato source and storage conditions. The potatoes used in the assay were size B Russet Burbank seed potatoes (averaging 3.4 oz.) obtained from Felix Zeloski Farms, Eagle River, Wis. Upon receipt mid-November, the potatoes were stored at 4° C. until treatment in January. Each treatment was cultivated in duplicate, and each duplicate was sprayed to 25 potatoes, such that 50 potatoes total were sprayed with each type of treatment. Each treatment was stored in 10 bundles of 5 potatoes per bundle. Bundles were wrapped first in a Wypall® (Kimberly-Clark) paper towel and then in a single layer of gauze, and tied at the top with a string and label. Six bundles were placed randomly in the vented polyethylene boxes described for the Fall TS #2 Peoria storage system. The storage boxes were arranged in six equal stacks in the incubator, which was controlled at 15° C. and 90–95% relative humidity. Potatoes were monitored after one month by measuring the length of the longest sprout.

Relative performance of treatments.

Table III gives the mean relative performances of strains across all four trials conducted at Parma and Peoria and indicates significant differences in treatment means upon statistical analysis of the treatments. Across test site variations in potato source and storage site conditions, the following five treatments were significantly better than the untreated control and similar to 16.6 ppm CIPC thermal fog: B-21050 (S11:T:07) cultivated on either SDCL or MDL; B-21133 (S11:P:12) cultivated on either SDCL or MDL; and B-21132 (S11:P:08) cultivated on MDL. The following three treatments had relative performance indices that averaged 61% higher than that of the untreated control, but they were not statistically different from the untreated control at the 95% confidence level, given its high standard deviation: B-21134 (S11:P:14) and B-21053 (P22:Y:05) cultivated on SDCL medium and B-21102 (S22:T:04) cultivated on MDL medium.

EXAMPLE 5

Impact of Viable Cells on Sprout Suppression

Experiment design.

In this study, the impact of washed viable cells of isolate B-21133 (S11P12) on sprout suppression was investigated. Washed viable cells were expected to be largely free of potentially bioactive extracellular metabolites that may be present in the fermented culture broth. The observation of sprout suspression by the washed bacteria treatments would reflect the bioactivity of the viable cells, as separate from the bioactivity of preformed metabolites that may be present in the whole fermented culture broth. Treatments sprayed to potatoes included an unfermented SDCL medium control (0 cells/ml), and washed cells of the bacterial antagonist formulated to concentrations of $4 \times 10^8$ and $8 \times 10_9$ viable cells in the fresh, unfermented SDCL medium, and a CIPC control.

Cell cultivation, harvest, transport, and storage.

Bacterial dry rot antagonist B-21133 (S11Pl2) was grown on SDCL medium according to the cultivation procedure of Example 2. Several culture replicas were harvested after 96 hours. Upon harvest, 800 mls of culture broth was centrifuged (10 min at 7000 rpm) to pellet cells. The cells were washed and resuspended in 100 ml of sterile phosphate buffer (Fisher Aid Pack®, USA, Gloucester, Mass.). The buffered cell suspension was again centrifuged to obtain cell pellets. The supernatant wash was decanted, and the cell pellet was resuspended in buffer to a turbidity of 100 absorbance units at 620 nm (corresponding to $8 \times 10^{10}$ viable cells/ml). The concentrated cell suspension was distributed equally among four sterile 20-ml crimp-sealed glass vials. The vials of cell concentrate and two 1-L bottles containing 600 ml of fresh, uninoculated SDCL medium were packed in a cooler with cold-packs to maintain temperature at 4–6° C. during overnight shipment from Peoria to the test site in Parma, Id. Upon arrival in Idaho, treatments were stored in a refrigerator until application on the next day. Just prior to spraying, the $4 \times 10^8$ and $8 \times 10^9$ cell/ml formulations were respectively prepared by mixing 1.5 mls of the cell concentrate with 298.5 mls of fresh, unfermented SDCL medium, and by mixing 30 mls of the cell concentrate with 270 ml of fresh, unfermented SDCL at 1.1 times normal strength (to compensate for the dilution from 270 to 300 ml final volume).

Potato Source.

The Yukon Gold potatoes used in this assay were harvested in May near Edison, Calif. The potatoes were washed and graded, but not subjected to chemical treatment, and finally carried by truck to Parma, Id. One hundred fifty pounds (165 kg; ~360 count) of potatoes were sprayed per treatment at a rate of 0.8 ml per potato. Controls for the experiment included unfermented SDCL medium and CIPC applied as a thermal fog at 525° F. for 5 minutes to achieve 16.6 ppm weight active ingredient per weight potato.

Potato storage and assessment.

Each treatment was distributed to ~36 mesh bags (10 tubers/bag) and stored in a 60-gallon ventilated barrel at 8° C. and 90–95% relative humidity. Loaded barrels were periodically ventilated: 3 hours fresh air flow at 0.50 scfm followed by 3 hours of no air flow. Sprouts were monitored monthly by removing 60 tubers (6 bags of 10 tubers) from each treatment barrel and rating the longest sprout length (LSL) per potato based on the 0–5 rating scale described in Example 2.

Results.

After 108 days of storage, potatoes treated with the two formulations of washed bacteria in unfermented SDCL medium were significantly less sprouted relative to the uninoculated, unfermented SDCL control (Table IV). The $4 \times 10^8$ cells/ml dosage of washed bacteria reduced sprouting by 8%, while the $8 \times 10^9$ cells/ml dosage reduced sprouting by 52%. By comparison, the CIPC control treatment reduced sprouting by up to 77% relative to the unfermented SDCL control and was significantly less sprouted than the other treatments. The relative sprout development of treatments was consistent through all four monitorings. Statistical separation of treatment means increased in significance throughout the storage period. These results indicate that washed viable bacteria, separated from the metabolite-bearing fermented culture broth, contribute significantly to sprout suppression.

EXAMPLE 6

Evaluation of Sprout Suppressiveness of Metabolites in Bacterial Production Cultures Experiment design.

Thin layer chromatography performed on culture harvests indicate that all deposit strains produce one or more metabolites during liquid cultivation. Some of the metabolites produced may have sprout inhibitory bioactivity. To evaluate this possibility, potatoes were treated with fermented SDCL culture broths that had been filtered to remove cells. Controls included no treatment, unfermented SDCL culture medium, and CIPC.

Summer 1997 Yukon Gold pilot trial.

Cultivation of strain B-21133 (S11:P:12) was carried out on SDCL medium and harvested after 96 h as described in Example 5. Cells were separated from the culture broth by centrifugation. The source of potatoes and methods of treatment transport, storage, and assessment were the sane as that used in the Parma pilot trial described in Example 5.

Fall Trial Season #3 Russet Burbank Laboratory Trial.

Cultivations of isolates on SDCL medium were performed and harvested after 96 h as described in Example 3.

Cells were separated from the culture broth using centrifugation to obtain cell pellets followed by 0.22 μm sterile filtration of the cleared supernatant broth to render it completely cell-free. The sterile-filtered broths were stored in the refrigerator (4–6° C.) until application to potatoes. The source of potatoes and methods of treatment storage and assessment were the same as that used in the Fall TS #3 Peoria Trial as described in Example 4.

Results.

The results listed in Table V indicate that in two trials utilizing two different potato cultivars, the cell-free fermented SDCL broth from cultures of B-21133 (S11:P:12) significantly decreased sprouting relative to the untreated and the unfermented SDCL controls by 17% and 21%, respectively. Among the five additional fermented SDCL broths applied to Russet Burbank potatoes, the fermented broth from B-21134 (S11:P:14) significantly reduced sprouting by 15% relative to the unfermented SDCL control; and two other broths from B-21132 (S11:P:08) and B-21050 (S11:T:07) reduced sprouting by 9% and 13%, respectively, relative to the unfermented SDCL control. The bioactivities of the cell-free fermented culture broths indicate that the majority of the deposit strains produce, during liquid cultivation, metabolites that play a role in potato sprout inhibition. The extent of bioactive metabolite production by any one isolate will depend on cultivation conditions. Strains that do not appear to produce sprout inhibitory metabolites under the cultivation conditions applied in this example may indeed produce them under other conditions found by standard optimization techniques and may additionally produce them on the potato surface.

EXAMPLE 7

Negligible Impact of Culture Media Ingredients on Sprout Suppression In the Absence of Sprout Control Agent Experiment design.

To study the impact of culture medium ingredients on sprouting, uninoculated, unfermented SDCL and MDL media were applied to washed potatoes. The experiment was repeated on two different potato cultivars, Russet Burbank and Russet Norkota. Russet Burbank potatoes from two different harvest seasons and at four different physiological ages were tested. Control treatments included sterile distilled water, pH 7 phosphate buffer (Fisher Aid-Pack®, USA Gloucester, Mass.), 10 ppm CIPC, and no treatment. Potatoes were washed as a precaution to eliminate the potential for interference due to resident microflora. If a resident microflora were presented a complete nutrient medium in the absence of a dominant population of dry rot antagonist, it is envisioned that its population growth could be stimulated to such an extent as to have significant impact on sprout development (in either a negative or positive direction).

Whole potato bioassays.

One day prior to use, potatoes were washed with gentle rubbing under a stream of cool tap water (chlorinated) and then rinsed with distilled water. Washed potatoes were allowed to dry ~30 minutes on Wypall® (Kimberly-Clark) paper towels before they were moved to 4° C. storage till use. The assay entailed spraying whole potatoes as described in the procedures given above for TS #1 and TS #3 trials conducted at Peoria. Three experiments were carried out with the TS #3 Wisconsin Russet Burbank potatoes which had been stored at 4° C. until treatment approximately 2, 3, and 4 months after harvest in October.

Potato eye core bioassays.

This assay was conducted using the same October TS #3-harvested Wisconsin Russet Burbank potatoes after ten months storage at 4° C. A second potato cultivar was also treated at the same time, and consisted of Russet Norkota potatoes which had been harvested in June 1998 near Edison, Calif. and stored only 2 months at 4° C. In this assay, treatments were applied to eyes that had been cored from the whole, washed potato using a stopper borer. Cores (1.1 cm dia.×2 cm) were moved to a sterile petri plate using care not to introduce cross-contamination. Five petri plates were stored in a plastic bag with a moistened paper towel in the bottom of the bag (40 mL water/towel). Bag tops were loosely closed to permit air exchange and refrigerated at ~4–6° C. for 7–10 days to allow the cores to suberize. One day before use, suberized potato cores were rinsed with sterile water, drained, and placed bud-end up in a sterile plastic 15-ml conical tube closed with a sterile cotton plug to allow air exchange. Racks of tubes and a wet paper towel were placed in loosely closed plastic bags and refrigerated at ~4–6° C. till use the next day.

The eye area of each core (2 g average weight) was coated with 12 $\mu$l of a given treatment. Ten replicates of each treatment were stored in the dark in cotton- plugged conical tubes, at 15° C., and 90–95% relative humidity.

A nondestructive measurement of total sprout length/core length was taken at two-week intervals. Tubes were not opened until the final monitoring after 4 weeks of storage. Sprout weight percent as 100×(sprout weight)/(core +sprout weight) was measured.

Results.

When applied to washed potatoes, there was no significant impact of unfermented MDL or SDCL medium ingredients on sprouting (Table VI). Thus medium ingredients alone were not contributing to sprout growth regulation. The proliferation of natural microflora residing on potato surfaces would be expected to be stimulated by the addition of nutrients, and such indigenous populations could contribute to random sprout growth regulatory effects when unwashed potatoes are treated with a nutrient medium. The application of a "sufficient" sprout-inhibitory biological control population by itself, or in combination with growth-supporting nutrients, allows favorable competition of the biocontrol agent with the natural microflora and direction toward the desired result of sprout inhibition, as demonstrated by Example 5.

EXAMPLE 8

Dry Rot Disease Control by Bacterial Treatments Demonstrating Sprout Suppression Experiment design.

In order to assess dry rot disease control in a parallel study, each of the twelve dry rot antagonist cultures that was tested in Examples 2–4 for sprout suppressiveness was also sprayed onto potatoes which had been treated with the dry rot causative pathogen, *Fusarium sambucinum*. Control treatments included unfermented MDL and SDCL media, pH 7 phosphate buffer (Fisher Aid-Pack®, USA Gloucester, Mass.), and 16.4 ppm thiabendazole (from Mertect® 340F containing 42% active ingredient). Thiabendazole (TB2) is the only chemical fungicide registered for use to control dry rot on potatoes destined for human consumption.

Pathogen and biocontrol agent inoculations.

Four thiabendazole-resistant strains of *F. sambucinum* (FMJ 1,2,3 and 4) were cultivated on CV8 agar plates incubated under 12 h light cycle at 25° C. After ca. one week of incubation, conidia were washed from an equal number of CV8 plates per each strain FMJ 1–4 and combined in phosphate buffer (Fisher Aid-Pack@, USA Gloucester, Mass.) to a concentration of about 5×10⁴/ml. The conidia suspension was sprayed to potatoes at a rate of 0.5 ml per average 3.4 oz tuber. The next day after conidia were applied, potatoes were wounded and treated with the 12 cultures of bacterial antagonists as previously described in Example 4 for the evaluation of sprout control in the TS #3 Peoria laboratory trial. Each treatment was cultivated in duplicate, and each duplicate was sprayed to 25 potatoes, such that 50 potatoes total were sprayed with each type of treatment.

Storage and monitoring of treated potatoes.

Each treatment was stored in 10 bundles of 5 potatoes per bundle, just as described in Example 4 for the TS #3 Peoria laboratory assessment of sprout control. Dry rot disease was assessed after 6 weeks of incubation by quartering potatoes and assigning a rating of 0 to 5, where 0 indicates that there is no diseased tissue, and 5 indicates a potato with 100% of the tissue showing disease; and so a potato rated as 1.5, for example, would indicate that 30% of the tissue was diseased.

Results.

As can be seen in Table VII, nine out of twelve bacterial treatments had mean disease ratings that were lower than that of the TBZ control. All six SDCL-grown inocula had mean disease ratings that were lower than the unfermented SDCL control, but only 3 of six MDL-grown inocula had disease ratings lower than the unfermented MDL control. The wounded potato disease assay which was employed in this study mimics the scenario by which potatoes are exposed to disease infection by wounding and also the scenario by which potatoes would be sprayed with biological control agent upon entering storage. Many factors (including random wounding, incomplete spray coverage, periderm coverage by soil, and others) contribute to high relative standard deviations in treatment means, especially when the level of disease is low. The high relative standard deviation coupled with the limited number of observations per treatment available in this experiment precluded statistical separation of individual treatment means. However, when treatments were grouped, the resulting increase in the degrees of freedom allowed statistical separation of superior versus inferior biological treatments. After treatments were ranked from best (lowest disease rating) to worst (highest disease rating), the membership of biological treatments in the grouping of best strains (Biological A) was expanded until the Biological A group mean failed to be significantly lower than the TBZ treatment mean. The remaining biological treatments were grouped in the "Biological B" group. Control treatments not containing either chemical or biological control agents were lumped as the "None" group of treatments. Section B of Table VII shows that seven of the twelve bacterial treatments tested (including five out of six bacterial strains) fell into the "Biological A" group. Among the seven treatments in the Biological A group, disease development in potatoes was reduced relative to the TBZ control by 29 to 86%. Biological Group A averaged a 59% reduction of disease relative to the none control and a 65% reduction relative to the TBZ control.

Among the seven superior treatments that fell into the Biological A grouping were four out of the five superior sprout control treatments shown in Table III. The superior treatments allowing dual sprout and dry rot control included: B-21133 (S11:P:12)+SDCL, B-21132 (S11:P:08)+MDL, B-21050 (S11:T:07)+MDL, B-21050 (S11:T:07)+SDCL. These results show that at least 3 out of 6 dry rot antagonistic bacteria can be cultivated and applied to potatoes such that significant levels of both disease and sprout control are accomplished. The results also show that the cultivation medium composition is important to the ability of strains to accomplish both sprout and dry rot control. For example, B-21133 (S11:P:12) grown on SDCL and B-21132 (S11:P:08) grown on MDL showed greater sprout and disease control bioactivities than did the same isolates grown on the other medium they were tested on. This finding suggests that appropriate optimization of cultivation medium, by anyone skilled in this art, may potentially allow all six strains to achieve significant levels of both dry rot and sprout suppression.

TABLE I (Example 1)
Impact of Six Bacterial Isolates on Sprout Development of Potatoes Stored 4 Weeks at 15° C.

| Isolate or Control Treatment | Cultivation[a] Medium | Mean[c] Sprout Number per Potato (±Standard Deviation) | Mean[d] Sprout Number per Potato Across Cultivation Media |
|---|---|---|---|
| B-21050 | MDL | 10.8 ± 2.1 | 10.0 AB |
| (S11:T:07) | SDCL | 9.6 ± 3.2 | |
|  | SMB | 9.6 ± 2.4 | |
| B-21102 | MDL | 10.8 ± 3.2 | 9.9 AB |
| (S22:T:04) | SDCL | 7.1 ± 1.7* | |
|  | SMB | 11.9 ± 3.4 | |
| B-21128 | MDL | 14.3 ± 5.1 | 12.2 A |
| (S09:3Y:08) | SDCL | 10.8 ± 2.1 | |
|  | SMB | 11.5 ± 2.5 | |
| B-21132 | MDL | 6.9 ± 6.2* | 6.3 C |
| (S11:P:08) | SDCL | 4.3 ± 5.2* | |
|  | SMB | 7.6 ± 3.8 | |
| B-21133 | MDL | 11.8 ± 2.2 | 7.3 BC |
| (S11 P:12) | SDCL | 0.0 ± 0.0* | |
|  | SMB | 10.1 ± 2.6 | |
| B-21134 | MDL | 10.1 ± 4.2 | 9.8 AB |
| (S11:P:14) | SDCL | 6.1 ± 3.0* | |
|  | SMB | 13.1 ± 4.2 | |
| Unfermented | MDL | 10.0 ± 3.2 | 11.5 A |
| Media Controls | SDCL | 12.0 ± 5.8 | |
|  | SMB | 12.5 ± 6.4 | |
| CIPC Control[b] |  | 6.3 ± 4.6* | 6.3 C |

[a]Cultivation medium abbreviations: MDL = Minimal Defined Liquid, SDCL = Semi-Defined Complete Liquid, SMB = Sabouraud Maltose Broth
[b]CIPC Control = 0.01 mg isopropyl N-(3-chlorophenyl) carbamate per g potato (10 ppm)
[c]Asterisks (*) designate means that are significantly less than 11.5, the average number of sprouts per potato observed across the three unfermented media controls.
[d]Within the column, means with no letters in common are significantly different (P ≤ 0.05) based on results of the Student-Newman-Keuls pairwise comparison method.

TABLE II

Pilot Demonstrations of Sprout Bioactivity of Six Bacterial Isolates Applied to Potatoes Stored at 8° C.[a]

| Treatment | | Example 2 Trial Season #2 Monitored in Mar. | | Example 3 Trial Season #3 Monitored in Apr. | |
|---|---|---|---|---|---|
| Isolate | Medium[b] | % Tubers not Peeping[c] | % Tubers OK for Freshpack[d] | LSL Rating[e] (0–5) | Sprout Weight[f] (%) |
| B-21050 | MDL | 40.0 AB | 70.0 ABC | 0.97 FG | 1.74 CD |
| (S11:T:07) | SDCL | 30.0 BCD | 60.0 A–D | 1.27 DEF | 2.55 BCD |
| B-21134 | MDL | 20.0 C–F | 76.7 ABC | 1.07 EFG | 2.52 BCD |
| (S11:P:14) | SDCL | 23.3 B–E | 53.3 B–E | 1.47 CDE | 2.47 BCD |

TABLE II-continued

Pilot Demonstrations of Sprout Bioactivity of Six Bacterial Isolates Applied to Potatoes Stored at 8° C.[a]

| Treatment | | | | Example 2 Trial Season #2 Monitored in Mar. | | | Example 3 Trial Season #3 Monitored in Apr. |
|---|---|---|---|---|---|---|---|
| Isolate | Medium[b] | % Tubers not Peeping[c] | % Tubers OK for Freshpack[d] | LSL Rating[e] (0–5) | Sprout Weight[f] (%) | | |
| B-21132 (S11:P:08) | MDL | 16.7 D–G | 60.0 A–D | 1.50 CDE | 1.57 D | | |
|  | SDCL | 0.0 G | 30.0 E | 2.20 B | — | | |
| B-21102 (S22:T:04) | MDL | 20.0 C–F | 66.7 ABC | 1.27 DEF | 2.29 BCD | | |
|  | SDCL | 20.0 C–F | 66.7 ABC | 1.27 DEF | 4.22 A | | |
| B-21133 (S11:P:12) | MDL | 23.3 B–E | 66.7 ABC | 1.30 DEF | 1.80 CD | | |
|  | SDCL | 53.3 A | 83.3 AB | 0.67 G | 3.26 AB | | |
| B-21053 (P22:Y:05) | MDL | 13.3 D–G | 60.0 A–D | 1.53 CDE | 2.70 ABC | | |
|  | SDCL | 6.7 EFG | 36.7 DE | 1.73 CD | 2.70 ABC | | |
| Controls | | | | | | | |
| CIPC Fog (16.6 ppm) | | 6.7 EFG | 86.7 A | 1.13 EFG | 2.39 BCD | | |
| CIPC Spray (10 ppm) | | — | — | — | 3.20 AB | | |
| Untreated | | 0.0 G | 26.7 E | 2.87 A | 4.24 A | | |

[a]Within columns, values with no letters in common are significantly different (P < 0.05) based on results of the Student-Newman-Keuls pairwise comparison method.
[b]Cultivation medium abbreviations: MDL = Minimal Defined Liquid, SDCL = Semi-Defined Complete Liquid, SMB = Sabouraud Maltose Broth
[c]Percent of tubers with longest sprout length (LSL) rating of 0.
[d]Percent of tubers with LSL rating of 0 to 1.
[e]The longest sprout length (LSL) rating scale was; 0 = no peeping or bulging; 1 = peeping/bud swelling up to 3 mm; 2 = sprouts 4 mm up to 1 cm; 3 = sprouts 1 cm up to 3 cm; 4 = 3 cm up to 5 cm; 5 = 5 cm or more.
[f]Sprout Weight % = 100 × (weight of sprouts)/(total weight of sprouts + potato).

TABLE III (Example 4)
Relative Performance Index Summary of Treatments and Controls Repeated at Parma and Peoria in Trial Seasons #2 and #3

| Treatment | Mean Relative Performance Index[a,b] | Standard Deviation |
|---|---|---|
| CIPC Spray (10 ppm) | 104.6 A | 53.6 |
| CIPC Fog (16.6 ppm) | 76.7 B | 21.9 |
| B-21050 (S11:T:07) ± MDL | 63.1 BC | 12.8 |
| B-21133 (S11:P:12) ± MDL | 54.7 BC | 10.8 |
| B-21050 (S11:T:07) ± SDCL | 54.7 BC | 11.4 |
| B-21133 (S11:P:12) ± SDCL | 53.7 BC | 19.6 |
| B-21132 (S11:P:08) ± MDL | 52.4 BC | 17.9 |
| B-21134 (S11:P:14) + SDCL | 45.8 BCD | 14.2 |
| B-21102 (S22:T:04) ± MDL | 45.8 BCD | 13.6 |
| B-21053 (S22:Y:05) ± SDCL | 45.7 BCD | 7.8 |
| B-21053 (S22:Y:05) ± MDL | 37.0 CD | 8.0 |
| B-21102 (S22:T:04) ± SDCL | 35.4 CD | 23.4 |
| B-21134 (S11:P:14) ± MDL | 34.6 CD | 27.3 |
| B-21132 (S11:P:08) ± SDCL | 32.5 CD | 25.0 |
| Untreated | 28.2 D | 34.1 |

[a]Within each trial site-monitoring date, treatment ratings were used to calculate the relative performance of each strain using the following statistical definition of Relative Performance Index (RPI): RPI = (2-F) × 100/4, where F = (treatment sprout rating − average of the treatment sprout ratings at the particular trial site and date)/the standard deviation of the treatment sprout ratings at the trial site and date. For a normally distributed data set, the value of F ranges between −2 and +2. Thus RPI values should fall between 0 (most sprouting) and 100 (least sprouting). The higher the RPI value for a given treatment, the better the sprout suppression. The mean RPI for a given treatment type was taken as the average of RPI across all trial site monitorings.
[b]Within columns, values with no letters in common are significantly different (P < 0.05) based on results of the Student-Newman-Keuls pairwise comparison method.

TABLE IV (Example 5)
Dosage Effect of Washed Viable Cells of B-21133 on the Sprout Development of Potatoes Stored at 8° C.

| Cells/mL in Unfermented SDCL[a] | Longest Sprout Length Rating (0–5)[b] Storage Day | | | |
|---|---|---|---|---|
|  | 31 | 53 | 69 | 108 |
| 0 | 0.38 AB | 1.80 A | 2.90 AB | 4.42 A |
| 4 × 10[8] | 0.42 A | 1.73 A | 2.80 B | 4.07 B |
| 8 × 10[9] | 0.25 B | 1.03 B | 1.72 C | 2.12 C |
| CIPC Fog (16.6 ppm) | 0.03 C | 0.65 C | 0.95 D | 1.00 D |

[a]Just prior to potato treatment, washed cells of the bacterial antagonist were formulated in fresh, unfermented SDCL medium. The 0 cells/mL treatment corresponds to a control consisting of only the uninoculated, unfermented SDCL medium.
[b]Within columns, values with no letters in common are significantly different (P < 0.05).

TABLE V (Example 6)
Sprout Inhibition Caused by Cell-free, Fermented SDCL Culture Broths[a]

| Treatment | California Yukon Gold Potatoes Stored at 8° C. LSL (0–5) | Wisconsin Russet Burbank Potatoes Stored at 15° C. LSL (mm) |
|---|---|---|
| Fermented SDCL Broths | | |
| B-21133 (S11:P:12) | 2.4 C | 31.8 C |
| B-21134 (S11:P:14) | — | 34.4 B |
| B-21132 (S11:P:08) | — | 35.2 ABC |
| B-21050 (S11:T:07) | — | 36.6 ABC |
| B-21053 (S22:Y:05) | — | 38.3 AB |
| B-21102 (S22:T:04) | — | 40.2 A |
| Controls | | |
| Unfermented SDCL | 4.4 A | 40.2 A |
| Untreated | 3.3 B | 38.0 AB |
| CIPC Fog (16.6 ppm) | 1.0 D | — |
| CIPC Spray (10 ppm) | — | 7.1 D |

[a]Within columns, values with no letters in common are significantly different (P < 0.05) based on the Student-Newman-Keuls pairwise comparison method.

TABLE VI (Example 7)
Impact of Unfermented Culture Medium Ingredients on Sprouting of Washed Potatoes

| Treatment | TS #1 Wisconsin Russet Burbank (Sprouts/tuber) | Whole Potato Bioassays TS #3 Wisconsin Russet Burbank LSL (mm) | | | Potato Eye Core Bioassays TS #3 Wisconsin Russet Burbank Sprout (% w/w) | TS #4 California Russet Norkota Sprout (% w/w) |
|---|---|---|---|---|---|---|
| | | Exp 1 | Exp 2 | Exp 3 | | |
| MDL | 10.0 A | — | — | — | 5.60 A | 2.00 A |
| SDCL | 12.0 A | 39.1 A | 21.3 A | 69.6 A | 6.06 A | 1.87 A |
| Water | 8.8 AB | — | — | — | 5.40 A | 2.69 A |
| Buffer | — | 40.2 A | 21.1 A | 67.9 A | — | — |
| Untreated | — | 39.0 A | 19.7 A | 66.4 A | 5.09 A | 1.58 A |
| CIPC | 6.3 B | 15.7 B | 7.2 B | 18.3 B | 0.05 B | 0.05 B |

Within columns, values with no letters in common are significantly different (P < 0.05) based on the Student-Newman-Keuls pairwise comparison method.

TABLE VII (Example 8)
Dry rot disease suppressiveness of biological treatment preparations for sprout control A. Disease ratings observed for each treatment

| Treatment | Mean Disease Rating (0–5) | Statistics Group |
|---|---|---|
| B-21053 (P22:Y:05) + SDCL | 0.050 | Biological A |
| B-21053 (P22:Y:05) + MDL | 0.053 | Biological A |
| B-21133 (S11:P:12) + SDCL | 0.074 | Biological A |
| B-21132 (S11:P:08) + MDL | 0.104 | Biological A |
| B-21102 (S22:T:04) + SDCL | 0.141 | Biological A |
| B-21050 (S11:T:07) + MDL | 0.207 | Biological A |
| B-21050 (S11:T:07) + SDCL | 0.253 | Biological A |
| B-21134 (S11:P:14) + SDCL | 0.300 | Biological B |
| B-21133 (S11:P:12) + MDL | 0.349 | Biological B |
| B-21134 (S11:P:14) + MDL | 0.361 | Biological B |
| B-21132 (S11:P:08) + SDCL | 0.380 | Biological B |
| B-21102 (S22:T:04) + MDL | 0.413 | Biological B |
| Unfermented SDCL | 0.429 | None |
| Unfermented MDL | 0.223 | None |
| Buffer | 0.251 | None |
| Thiabendazole (TB2) | 0.355 | TBZ |

B. Statistical analysis of treatment groups

| Statistics Group | Mean Group Disease Rating (0–5) |
|---|---|
| Biological A | 0.123 A |
| Biological B | 0.361 B |
| None | 0.297 B |
| TBZ | 9.355 B |

[a]Within columns, values with no letters in common are significantly different (P < 0.05) based on results of the Student-Newman-Keuls pairwise comparison method.

We claim:

1. A method for suppressing sprouting of a potato tuber in storage comprising:

applying to the surface of said potato tuber a sprout control agent comprising at least about 0.05 ml of a whole culture broth containing at least about $1 \times 10^8$ viable cells/ml of a sprout-suppressing bacterial isolate, wherein said isolate is a bacterium selected from the group consisting of *Pantoea agglomerans* NRRL B-21048, *Pseudomonas corrugata* NRRL B-21049, *Enterobacter cloacae* NRRL B-21050, *Pseudomonas corrugata* NRRL B-21051, *Pseudomonas fluorescens* bv.V NRRL B-21053, *Enterobacter* sp. NRRL B-21101, *Pseudomonas fluorescens* bv.I NRRL B-21102, *Enterobacter* sp. NRRL B-21103, *Pantoea* sp. NRRL B-21104, *Pseudomonas corrugata* NRRL B-21105, *Pseudomonas fluorescens* bv.I NRRL B-21128, *Pseudomonas corrugata* NRRL B-21129, *Enterobacter* sp. NRRL B-21132, *Pseudomonas fluorescens* bv.V NRRL B-21133, *Pseudomonas fluorescens* bv.V NRRL B-21134, *Pseudomonas fluorescens* bv.V, NRRL B-21135, *Pseudomonas corrugata* NRRL B-21136 and *Pseudomonas fluorescens* bv.V NRRL B-21137; and wherein sprouting is suppressed when holding said potato tuber in storage for a period of time in excess of that for which sprouting of said potato tuber would occur under storage conditions in the absence of applying the sprout control agent.

2. The method of claim 1 wherein said sprout control agent is applied after wounding and wound healing has occurred.

3. The method of claim 1 wherein said sprout control agent is applied to potato tubers that are not susceptible to fungal potato dry rot.

4. The method of claim 1, wherein said isolate is *Enterobacter cloacae* NRRL B-21050.

5. The method of claim 1, wherein said isolate is *Pseudomonas fluorescens* bv.I NRRL B-21102.

6. The method of claim 1, wherein said isolate is *Pseudomonas fluorescens* bv.I NRRL B-21128.

7. The method of claim 1, wherein said isolate is *Enterobacter* sp. NRRL B-21132.

8. The method of claim 1, wherein said isolate is *Pseudomonas fluorescens* bv.V NRRL B-21133.

9. The method of claim 1 wherein said isolate is *Pseudomonas fluorescens* bv.V NRRL B-21134.

10. The method of claim 1, wherein said isolate is *Pseudomonas fluorescens* bv.V NRRL B-21053.

* * * * *